United States Patent [19]

Karbach et al.

[11] Patent Number: 5,485,751
[45] Date of Patent: Jan. 23, 1996

[54] METHOD FOR LONGITUDINAL, TRANSVERSE AND OBLIQUE ERROR TESTING OF WORK PIECES BY MEANS OF ULTRASOUND, ACCORDING TO THE IMPULSE-ECHO METHOD

[75] Inventors: Bernhard Karbach, Erftstadt-Friesheim; Ottokar Patzke, Erftstadt-Liblar, both of Germany

[73] Assignee: Firma Krautkrämer GmbH & Co., Germany

[21] Appl. No.: 81,615

[22] Filed: Jun. 23, 1993

[51] Int. Cl.⁶ .................................................. G01N 29/04
[52] U.S. Cl. .................................................. 73/618; 73/620
[58] Field of Search ........................... 73/618, 619, 620, 73/622

[56] References Cited

U.S. PATENT DOCUMENTS

| | | | |
|---|---|---|---|
| 4,307,612 | 12/1981 | Elsley et al. | 73/620 |
| 4,455,872 | 6/1984 | Kossoff et al. | 73/618 |
| 5,335,547 | 8/1994 | Nakajima et al. | 73/620 |

FOREIGN PATENT DOCUMENTS

| | | | |
|---|---|---|---|
| 0131371 | 1/1985 | European Pat. Off. . | |
| 4036005 | 5/1992 | Germany . | |
| 9208970 | 11/1990 | WIPO . | |
| WO92/08970 | 5/1992 | WIPO . | |

Primary Examiner—Hezron E. Williams
Assistant Examiner—Max Noori
Attorney, Agent, or Firm—Quarles & Brady

[57] ABSTRACT

The method for ultrasonic testing of work pieces to detect longitudinal, transverse and oblique errors therein uses a test head support having at least one test head. The test head support is moved in a translatory direction along a surface of the work piece. Ultrasonic impulses are generated in a rapid sequence by the test head, progress along a sound beam, and are directed to impact the surface of the work piece in test areas. All test areas of the at least one test head lie in a linear test path. In the case of uninterrupted, translatory movement, all test areas meet in one and the same test area. The sound beams progress in a given constant angle in relation to one set perpendicular line on each test area. The sound beams rotate, in a conical envelope, around the respective perpendicular line. A complete rotation of 360° takes place in time $t_r$ which is shorter than time $t_t$ which is required by the translatory movement in order to cross a distance with the dimensions of a test area, per revolution generates and sounds at least ten ultrasound impulses into the surface of the work piece.

12 Claims, 3 Drawing Sheets

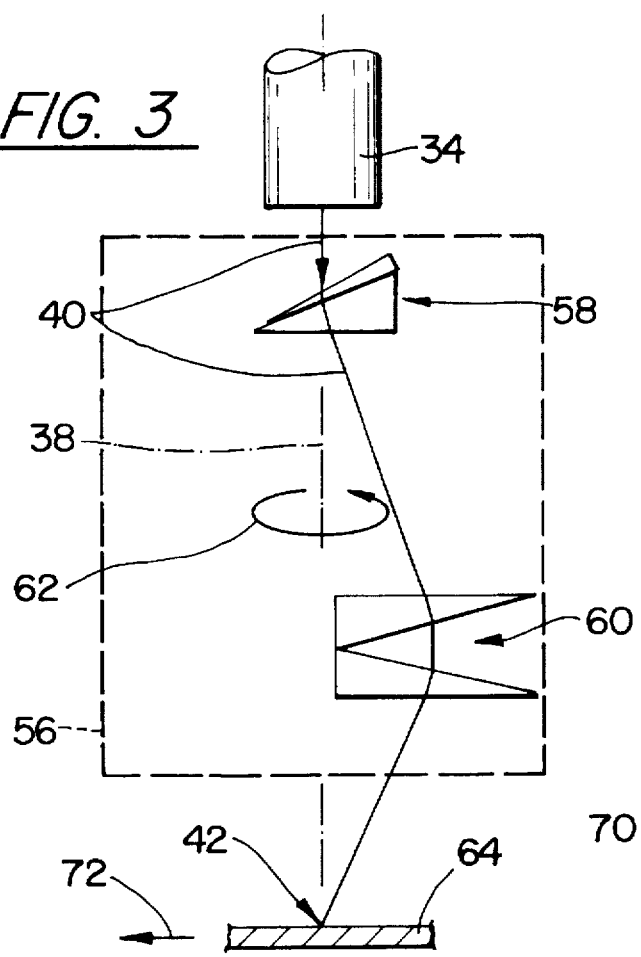
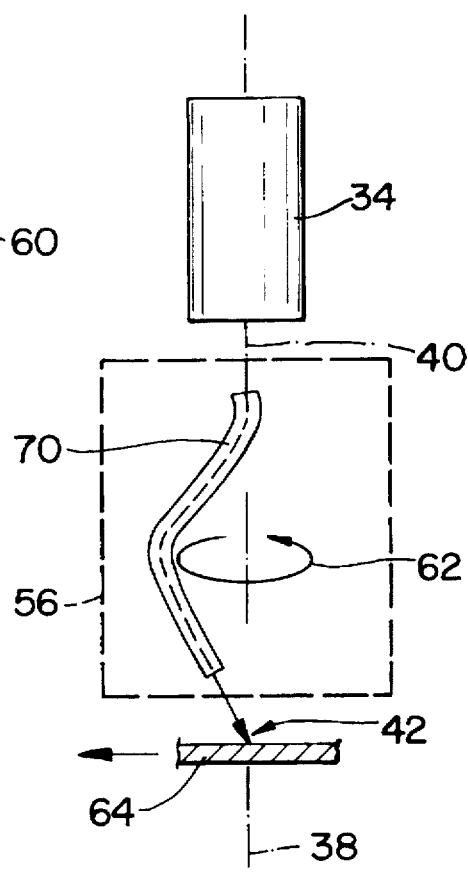
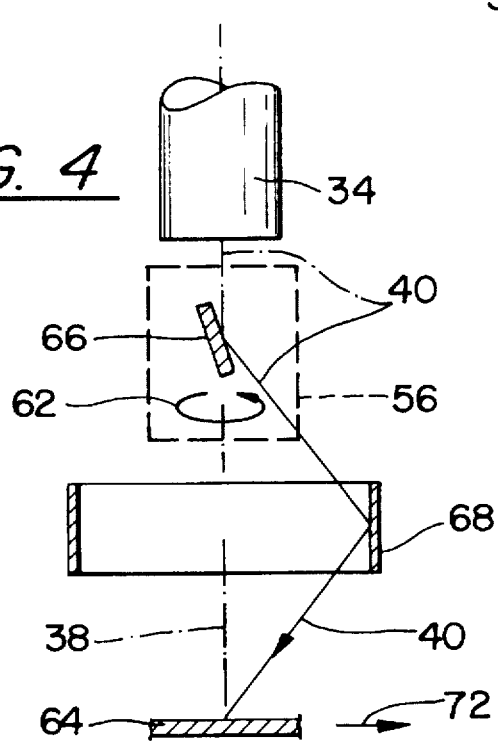

METHOD FOR LONGITUDINAL, TRANSVERSE AND OBLIQUE ERROR TESTING OF WORK PIECES BY MEANS OF ULTRASOUND, ACCORDING TO THE IMPULSE-ECHO METHOD

FIELD OF THE INVENTION

The invention relates to a method for longitudinal, transverse and oblique error testing of work pieces by means of ultrasound, by which a test head support, which features at least one test head, is moved in a translatory manner along the surface of the work piece and ultrasound impulses are generated in rapid succession, which impact onto the surface of the workpiece from each test head along a sound beam in test areas, whereby all of these test areas are on a linear test path, so that in the case of interrupted translatory movement all test areas in one and the same test area are integrated, and whereby the sound beams run at a predetermined, constant angle onto a perpendicular line established at each test area. In particular, there is the advantage of determining all oblique error positions between the longitudinal and transverse position in one test cycle.

BACKGROUND OF THE INVENTION

From DE 40 36 005 A1 a method of this type is known, by which the work pieces which are to be tested are rotationally symmetrical, that is, pipes and rods in particular. According to this known method oblique errors in the work piece which lie within a pregiven angular range can be specifically sensed. Each test head support has two test heads which form a pair and which are aligned toward a common test area on the surface of the workpiece. The sound beams of these two test heads are symmetrical in relation to a respective perpendicular line, which is established on the test area. One test head of the pair senses oblique errors in a positive angle range, while the other test head senses the oblique error with the same value, but in the negative angle range.

The known test head support can be rotationally adjusted, therefore oblique errors in a desired orientation can be sensed.

From EP 131 371 A1 an ultrasound test device is known, by which a test head support is rotated by means of a motor, and in which one test head is arranged at an angle to the axis of rotation.

With the known devices and methods as applied, it is not possible to check whether a workplace is free of oblique errors of any type. At the present time such tests are not prescribed by the standards and therefore are not performed, but it is becoming increasingly more important to test selective sample pieces, and possibly entire production series, in order to ascertain that no oblique errors exist at any angular position.

SUMMARY OF THE INVENTION

The invention comes into play at this point. It has the goal of further enhancing the known method of the type indicated previously in such a way that angle errors at any angular position can be sensed.

Beginning with the characteristics of the method of the type indicated previously, this task is accomplished by a method exhibiting the features of patent claim 1.

According to the invention any individual test area can be checked for angle errors in different positions; for this, at least ten measurements are performed with different single sound angles at an always constant angle to the respective line running perpendicular to the test area. The change of angles in this case is so rapid, as compared to the translatory movement of the test head support across the work piece, that a measurement of all angle positions, i.e. a rotation of 360° has been carried out, has taken place before the translatory movement has shifted the test area to the extent that it no longer overlaps, not even at least partially, with the test area at the beginning of the angle measurement. By means of at least ten measurements per revolution it is assured that an angular resolution of at least 36° is obtained, which is sufficient to detect oblique errors of the most diverse orientation.

The method according to the invention features the advantage that all oblique error positions in a test cycle between the longitudinal, transverse and oblique position can be determined. The words oblique error or angle error are used in the following for all error positions in the longitudinal, transverse and oblique directions and are intended in a descriptive sense.

The term test area is intended to refer to the spot at which an, evaluation can be made with a single impulse echo measurement. The test area, also referred to as the test spot, is, for example, defined by a −6 dB (or −10 dB) drop off in the verification sensitivity, starting from the central sound beam. The test area is typically a circular spot, the diameter of which is usually between 2 and 4 mm. The actual values are dependent of the type of test head used, the focusing, the distance of the test head from the surface, and so on. The indicated values should only generate a reference point.

It has been proven advantageous to use as few test heads as possible while implementing the method, since the apparatus is expensive, and thereby the total costs of an installation can be reduced. For this purpose, at least one test head with its test head support rotates around an axis which runs parallel to the perpendicular line on the test area. The test head itself is set at an angle and sends out beams at an angle of normally 19° onto the surface of the work piece.

In this regard the mechanical and electronic expenses are less and the test speed can be increased if more than one test head is used, for example two, three or more test heads at the same gradation angles. A particular advantage has been demonstrated when a circular arrangement of test heads is provided, said heads being controlled in succession. In this case the relative mechanical movement is considerably simplified.

Finally, it has been shown to be advantageous to provide reflectors, refractors or sound conductors between a non rotated test head and the work piece surface, these being arranged such that the individual sound signals from the various directions are beamed onto the workpiece, and their echoes are recorded.

The method can, in particular, be applied for test devices for round materials, that is pipes and rods, as well as for plate shaped materials, that is, in particular, sheet metal. In the first case the translatory movement can be carried out on a spiral line by turning the pipe or the rod around its longitudinal axis and by a longitudinal feed, or through a rotor and by a longitudinal feed of the rotationally symmetric test piece; for this purpose reference is made to the already previously indicated DE 40 36 005 A1. With a rotor, the rotor drive can be applied simultaneously by means of suitable gearing and coupling, for the rotating drive of a test head support.

With circular arrays it has been shown to be advantageous to adhere a planar oscillation ring to a damping body ring, and then to subsequently subdivide it into individual oscillators with predetermined gradation angles. The sound angle of generally 19° is obtained through a preadhered lens ring.

With such an arrangement or with at least two single test heads a sounding is also possible for any angular direction.

BRIEF DESCRIPTION OF THE DRAWINGS

Other advantages and characteristics of the invention can be derived from the remaining claims as well as from the description of the embodiments that follows, which is not to be understood as limiting, and in which the method according to the invention is explained in more detail. Shown in the drawings are:

DETAILED DESCRIPTION OF THE PREFERRED EMBODIMENTS

Figure 1:
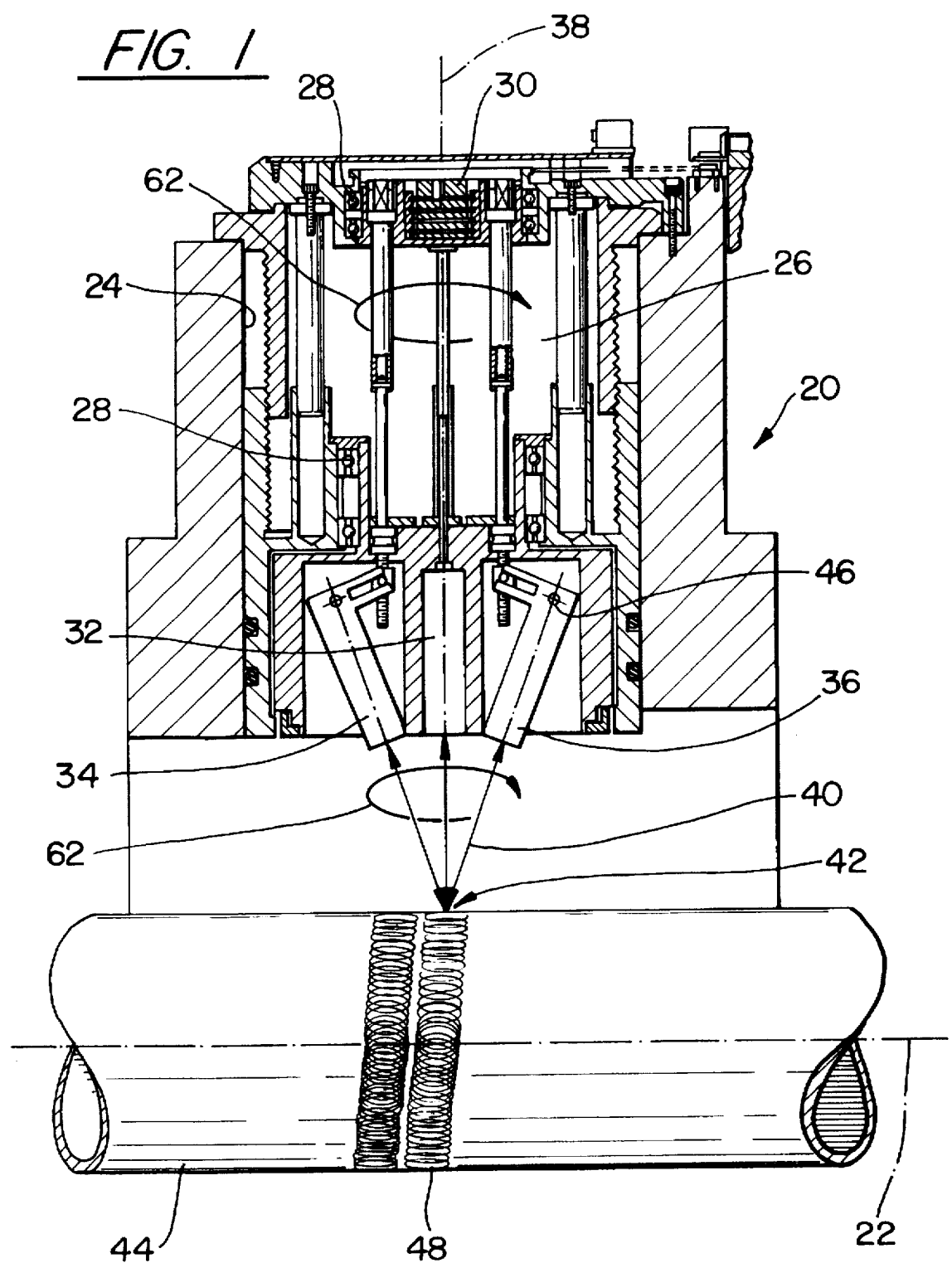
FIG. 1, a sectional illustration through the partial area of a rotor of a rotary test machine for pipes, with the illustration of a tested, partial section of a pipe, the sectional plane running through the longitudinal axis of the pipe, FIG. 2, a sectional view of a pipe test machine with a circular array of test heads, the sectional plane runs in a plane of the diameter of the pipe, FIG. 3, a basic illustration in lateral view of an arrangement for implementing the method according to the invention, in an application for sheet metal testing, the arrangement functions according to the principle of sound refraction, FIG. 4, a basic illustration in lateral view of an arrangement for implementing the method according to the invention, in an application for sheet metal testing, the arrangement functions according to the principle of sound reflection and, FIG. 5, a basic illustration in lateral view of an arrangement for implementing the method according to the invention, in an application for sheet metal testing, the arrangement functions according to the principle of sound conduction in a pipe.

In FIG. 1 a partial area of a rotor 20 of a pipe test machine is shown, the rotor rotates around a rotational axis 22 and has a radial bore 24 into which a test insert is emplaced. This consists of an outer part and an inner test head support 26, stationary with respect to the bore 24. The outer part, as such, is known, and no further details need be presented here in this regard, the test head can be adjusted by rotation and it can be adjusted longitudinally in the radial bore 24. The test head is connected to the test head support 26 by means of two sets of bearings 28; furthermore, it supports the stator of a collector ring system 30 that serves to transfer the electrical signal.

The test head support 26 is essentially constructed rotationally symmetrical. On its lower, free end there are a total of three test heads 32, 34, 36, also referred to as ultrasound transducers, that are freely accessible. The test head 32 is a central test head which is arranged at the radial bore 24 on the axis 38, which is also the rotational axis of the test head support 26. Both other test heads 34, 36 are arranged in a V-shape relative to each other. The arrangement is such that all central beams 40 of the three test heads 32 to 36 meet at a single point 42. This point 42 is located on the surface of a pipe 44 which is to be tested, the pipe axis of which coincides with the rotation axis 22. It is moved longitudinally in the direction of this rotation axis 22. This leads, together with the rotational movement of the rotor 20 around the rotational axis 22, to a spiral shaped scan path for the ultrasound measurement on the outer wall of the pipe 44. Expressed in another way, the point 42 drifts along a helical line during testing, along the outer wall of the pipe. The angle of inclination at which the two lateral test heads 34, 36 are placed relative to the axis 38 is adjustable. For this, a spindle is provided in each test head support 26, said spindle being rotationally adjustable from outside and fixed in place, with a nut resting on said spindle, which in turn engages in a longitudinal slot provided on the test head 34 or 36. The test heads 34, 36 are swivelably arranged around an axis 46.

Each test head 32 to 36 creates a test spot on the surface of the pipe 44 which is to be tested, said spot in general is arranged centrally around the point 42 where the central beam 40 impacts the surface, and it has a diameter of, for example, 3 mm. This test spot rotates around the axis 38, as a result of the rotation of the test head support 26 around the axis 38. The three test spots 48 of the three test heads 32 to 36 thereby rotate together on the basis of the common mechanical arrangement.

At the same time the test spots 48 are guided along the already specified helical path along the surface of the pipe 44. Overall, this results in a superimposed movement, such as is shown in FIG. 1, due to the intertwined circular paths, which are arranged in close proximity next to each other. These circular paths limit the respective test spot 48. Each circular path should represent a complete rotation of the test head support 26 around 360°. During this complete rotation at least ten measurements take place, that is, from both lateral test heads 34, 36 in total at least ten ultrasound impulses are given off and then received. With any sounding, at least ten pulses are emitted and received by the other test head 34 or 36; in the case of a separate measurement, each of the two test heads 34 or 36 emits at least, in total, five ultrasound impulses per a rotation of 360°, and receives their echoes.

As is evident from FIG. 1, the circular paths twisted closely inside each other are so close together that, after a complete rotation, the shift in the circumferential direction of the pipe is smaller than the diameter of the respective circular path. This means that a full rotation of the test spot 48 takes place, before the translatory movement, which occurs through the rotation of the rotor 20 around its rotation axis 22, and can further shift the test spot 48 by a distance which corresponds to the diameter of the test spot 48. In the illustration, approximately 5 complete rotations of the test head support 26 of 360° take place before the translatory movement has caused a shift of the test spot by an area which corresponds to the diameter of the test spot 48. Thus, it is assured that at each point 42 a complete recording of errors is possible in all angular positions, before the test moves on in a translatory direction.

Viewed from point 42 on the outer wall of the pipe 44, the central beams 40 and therefore also the sound beams enveloping these (concentrically enveloping) from the lateral test heads 34, 38 rotate on a conical wall, the axis of which is perpendicular to the pipe surface, established at point 42. It coincides with the axis 38.

The rotational drive for the test head support 26 results either by means of a separate electric motor or a stationary ring gear which envelops the rotor 20 on the outside and from which a rotational drive of the test head support 26 is created by means of an intermediate gear box. The solution first indicated has the advantage that the turning speed at which the test head support 26 rotates around its axis 38 can be more easily adjusted with regard to the translatory movement. Furthermore, in the case of a separate drive it is simpler to switch between a synchronized movement of the rotation and the translation, and a non synchronized movement. Usually, synchronization is used so that, for each individual rotation of the test spot 48 by 360°, the ultrasound tests are performed at specified angles, for instance starting at 0 degrees (coinciding with the longitudinal axis of the pipe) at 36°, 72°, 108°, etc., i.e. every 36°. But it can also be performed at every second rotation, for example shifted by 18°, so that intermediate areas are being measured every second test. However, it is also possible to perform a test without any synchronization whatsoever, which is, for instance, expedient if the absolute position of the oblique errors are not of interest, but rather only the recording of any oblique errors.

Figure 2:
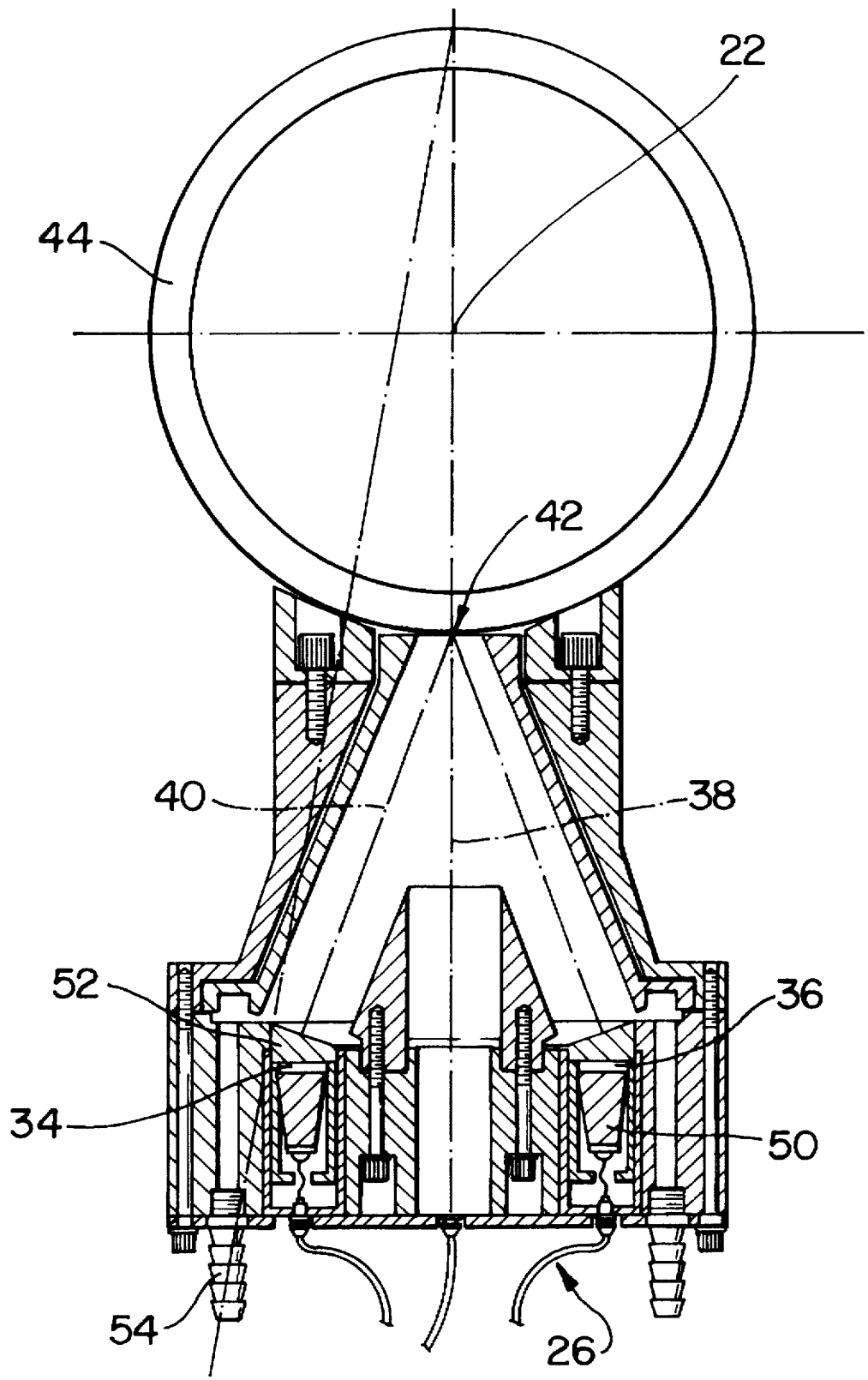

FIG. 2 shows a test machine with a stationary test arrangement. A pipe 44 to be tested is moved underneath the test arrangement in a helical manner. It is, however, also possible to install a test arrangement of this type in a rotor according to the representation in FIG. 1.

Contrary to the embodiment in FIG. 1, the test arrangement is now stationary, that is, it is not mechanically turned around the axis 38. This is accomplished by the fact that, instead of two lateral test heads 34, 36, a ring of test heads 34, 36 is used, consisting of ten ring sectors. These are adhered onto a rear damper body 50 which is also circular. At their front they feature wedge shaped rings 52 which cause a fracture of the sound beam, as is shown by the central beam 40. Preferably at least one ring 52 consists of ring sectors which can be adjusted individually, thereby the central beams 40 of the ten individual oscillators can be adjusted to one single point 42.

During the practical performance of the test the pipe 44 is moved, longitudinally with regard to its axis 22, from and into the plane of the paper at the same time as the pipe is turned around this axis 22. The space in front of the test heads 34, 36, which is essentially cone shaped, is filled with water by means of water connections 54, and in this manner the necessary water coupling occurs, as is also present in the exemplified according to FIG. 1. In the case of the embodiment according to FIG. 2, it is possible to work with pool technology.

In the exemplified embodiment according to FIG. 3 a test head 34 is provided, the central beam 40 of which coincides with the axis 38. The test head 34 is stationary. Below the test head, coupled by means of water, there is a container 56 in which 2 cone shaped prism systems 58, 60 are arranged, which are in the water and fixed in the container 56. The prisms rotate, together with the container, in the direction of the arrow 62 around the axis 38. The upper prism system 58 thereby causes a deviation of the central beam 40 and thereby of the entire sound beam surrounding this central beam 40, from the direction of the axis 38. The lower prism system 60 corrects this deviation so that the central beam 40 sections the axis 38 at point 42. This point 42 coincides with the surface of a workpiece which, in this case, is sheet metal 64.

The central beam 40 rotates on a conical wall as a result of the rotation of the upper prism system 58. In the displayed, exemplified embodiment the lower prism system 60 is also rotated, but this, in principle, is not necessary. This prism system 60 can also be substituted by a turning device which is created if the prism system shown is turned around the axis 38. In this case the lower prism system 60 can remain stationary.

Along the sound path from the test head 34 to the work piece (sheet metal 64) a water path is formed, for example by filling the container 56 and coupling the sheet metal 64 through pool technology or by means of a water jet. It is also possible to fill the container with a solid body, such as a plastic material.

In the exemplified embodiment according to FIG. 4 the central beam 40, and therefore the entire sound beam from a single test head 34, reaches the surface of an upper reflector 66 which is in a container 56, and turns with the container in the direction of the arrow 62. In this case the container 56 is also filled with water.

The deflected central beam 40, which rotates on a conical wall, then reaches the inner area of a cylindrical reflector 68 and from there is again refracted in such a way that it sections the axis 38 which coincides with the central beam 40 of the test head 34. The point of sectioning is point 42, which in turn coincides with the surface of a work piece to be tested, which is sheet metal 64.

In the exemplified embodiment according to FIG. 5, a single stationary test head 34 is also provided. A central beam 40 impacts a sound conductor 70 which is filled with water, along the axis 38. In the exemplified embodiment shown, it is surrounded by a container 56 which itself can be filled with water, but this is not necessary.

The sound conductor 70 consists of a pipe. This pipe is turned around the axis 38 in the direction of the arrow 62. The upper entry area of the sound conductor 70 runs in the direction of axis 38. From there the sound conductor 70 bends toward the outside and thereafter extends into a counter curve in such a way that a lower emitting area is directed toward axis 38. A sound beam guided in this pipe shaped sound conductor 70 leaves the sound conductor 70 in the direction of the central beam 40 and impacts onto the surface of sheet metal 64 at a point 42 which is the point of sectioning of the axis 38.

Instead of a pipe shaped sound conductor 70, a solid material may be selected, for instance having a rectangular cross section.

The exemplified embodiments according to FIGS. 3 to 5 include the advantage that the test head 34 need not be rotated. The turned parts are non electrical parts, the turning movement can be easily coupled to the stationary parts by means of water paths. Therefore, the mechanical requirements for rotation around the axis 38 and in the direction of the arrow 62 are reduced.

During testing, the translatory movement of sheet metal 64 takes place in the direction of the arrow 72. Instead of sheet metal, another work piece, such as a pipe, can also be tested. Thus, the arrangements according to FIGS. 3 to 5 can be arranged in a rotor of a rotary test machine.

We claim:

1. Method for longitudinal, transverse and oblique error testing of work pieces, by which a test head support (26) featuring at least one test head (32 to 36) is moved in a translatory direction along the surface of the work piece (44, 64) and where ultrasound impulses are generated in a rapid sequence, which, coming from each test head (32 to 36) impact the surface of the work piece (44, 64) along a sound beam in test areas on the surface of the work piece (44, 64) whereby all of these test areas lie in a linear test path, so that in the case of uninterrupted, translatory movement, all test areas meet in one and the same test area, and whereby the sound beams progress in a given constant angle in relation to one set perpendicular line 38 on each test area, whereby
a) the sound beams rotate, on a conical wall, around the respective perpendicular line, 38 forming an axis, b) complete rotation of 360° takes place in time $t_r$ which is shorter than time $t_t$ which is required by the translatory movement in order to cross a distance with the dimensions of a test area, and c) per revolution generates and sounds at least ten ultrasound impulses into the surface of the work piece (44, 64).

2. Method according to claim 1, characterized by the fact that during the rotation of the sound beams around the respective perpendicular line 38, the ultrasound impulses are generated in equal gradation angles.

3. Method according to claim 1 characterized by the fact that the test head support (26) turns around the respective perpendicular line (38).

4. Method according to claim 1, characterized by the fact that the test head support (26) features test heads (43, 36) arranged on a ring around the respective perpendicular line 38, and which preferably features test heads (34, 36) immediately adjacent to each other (circular array).

5. Method according to claim 1, characterized by the fact that at least one test head (34) is moved in the translatory direction, that the ultrasound impulses are sounded, via reflectors, (66, 68) on the surface of the work piece (44, 64) and that the echoes of said ultrasound impulses off of said surface of the work piece (44, 64) are received by means of these reflectors (66, 68), and that at least one reflector is turned circumferentially around said axis 38.

6. Method according to claim 1, characterized by the fact that at least the one test head (34) is moved in the translatory direction only, that the ultrasound impulses of this test head (34) are sounded by means of refractors (prism systems 58, 60), to the surface of the work piece (44, 64), and that the echoes of said ultrasound impulses off of said surface of the work piece (44, 64) are received by means of these refractors and that at least one refractor (prism system 58) is turned circumferentially around said axis (38).

7. Method according to claim 1, characterized by the fact that at least the one test head (34) is moved in the translatory direction only, that there is a sound conductor (70) between the test head (34) and the work piece (44, 64), said sound conductor 70 rotating circumferentially around the axis (38) and that this sound conductor (70) has a receiving area running along said axis (38) and an emitting area running at an angle to this axis 38.

8. Method according to claim 2, characterized by the fact that the test head support (26) turns around the respective perpendicular line (38).

9. Method according to claim 2, characterized by the fact that the test head support (26) features test heads (43, 36) arranged on a ring around the respective perpendicular line 28, and which preferably features test heads (34, 36) immediately adjacent to each other (circular array).

10. Method according to claim 2, characterized by the fact that at least the one test head (34) is moved in the translatory direction, that the ultrasound impulses are sounded, via reflectors, (66, 68) on the surface of the work piece (44, 64) and that the echoes of said ultrasound impulses off of said surface of the work piece (44, 64) are received by means of these reflectors (66, 68), and that at least one reflector is turned circumferentially around said axis 38.

11. Method according to claim 2, characterized by the fact that at least the one test head (34) is moved in the translatory direction only, that the ultrasound impulses of this test head (34) are sounded by means of refractors (prism systems 58, 60), to the surface of the work piece (44, 64), and that the echoes of said ultrasound impulses off of said surface of the work piece (44, 64) are received by means of these refractors and that at least one refractor (prism system 58) is turned circumferentially around said axis (38).

12. Method according to claim 2, characterized by the fact that at least the one test head (34) is moved in the translatory direction only, that there is a sound conductor (70) between the test head (34) and the work piece (44, 64), said sound conductor 70 rotating circumferentially around the axis (38) and that this sound conductor (70) has a receiving area running along said axis (38) and an emitting area running at an angle to this axis 38.

* * * * *